(12) United States Patent
Kim et al.

(10) Patent No.: US 10,028,674 B2
(45) Date of Patent: Jul. 24, 2018

(54) ULTRA-LOW-FIELD NUCLEAR-MAGNETIC-RESONANCE DIRECT MYOCARDIAL ELECTRICAL ACTIVITY DETECTION METHOD AND ULTRA-LOW-FIELD NUCLEAR-MAGNETIC-RESONANCE DEVICE

(71) Applicant: KOREA RESEARCH INSTITUTE OF STANDARDS AND SCIENCE, Daejeon (KR)

(72) Inventors: Kiwoong Kim, Daejeon (KR); Yong-Ho Lee, Daejeon (KR); Jin-Mok Kim, Daejeon (KR); Hyukchan Kwon, Daejeon (KR); Kwon Kyu Yu, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 1625 days.

(21) Appl. No.: 13/891,533

(22) Filed: May 10, 2013

(65) Prior Publication Data
US 2013/0241551 A1 Sep. 19, 2013

Related U.S. Application Data

(63) Continuation of application No. PCT/KR2011/004178, filed on Jun. 9, 2011.

(30) Foreign Application Priority Data

Nov. 23, 2010 (KR) .................. 10-2010-0116596

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0044* (2013.01); *G01R 33/24* (2013.01); *G01R 33/445* (2013.01)

(58) Field of Classification Search
CPC ...... A61B 5/055; A61B 5/0044; G01R 33/24; G01R 33/445
See application file for complete search history.

(56) References Cited

U.S. PATENT DOCUMENTS 6,522,908 B1 * 2/2003 Miyashita ............ A61B 5/0064
600/409
8,044,663 B2 * 10/2011 Kim ...................... G01N 27/76
324/309
(Continued)

FOREIGN PATENT DOCUMENTS

JP 11-121221 4/1999
JP 2002-028144 1/2002
(Continued)

OTHER PUBLICATIONS

Guillemaud et al., "Estimating the Bias Field of MR Images", IEEE Transactions on Medical Imaging, vol. 16, No. 3, Jun. 1997, p. 238.*
(Continued)

*Primary Examiner* — Dixomara Vargas
(74) *Attorney, Agent, or Firm* — Jenkins, Wilson, Taylor & Hunt, P.A.

(57) ABSTRACT

Provided are ultra-low-field nuclear-magnetic-resonance myocardial electrical activity detection method and an ultra-low-field nuclear-magnetic-resonance device. The ultra-low-field nuclear-magnetic-resonance device includes magnetic shielding room; a high-sensitivity magnetic field sensor disposed adjacent to a measurement target disposed inside the magnetic shielding room; and a bias magnetic field generating coil for providing an external measurement
(Continued)

bias magnetic field, corresponding to a proton magnetic resonance frequency (nuclear magnetic resonance frequency) corresponding to a frequency of periodic myocardial activity of a lesion desired to be measured, to the measurement target. The high-sensitivity magnetic field sensor measures a magnetic resonance signal generated from the measurement target.

3 Claims, 4 Drawing Sheets

(51) Int. Cl.
    *G01R 33/24*     (2006.01)
    *G01R 33/44*     (2006.01)

(56) References Cited

U.S. PATENT DOCUMENTS

| | | | |
|---|---|---|---|
| 9,903,925 B2 * | 2/2018 | Kim | G01R 33/36 |
| 2009/0295390 A1 * | 12/2009 | Hahn | G01R 33/326 324/318 |
| 2010/0090697 A1 | 4/2010 | Savukov et al. | |

FOREIGN PATENT DOCUMENTS

| | | |
|---|---|---|
| JP | 2006-075403 | 3/2006 |
| JP | 2009-273815 | 11/2009 |
| KR | 1020090128735 | 12/2009 |
| WO | WO 2012/070738 | 5/2012 |

OTHER PUBLICATIONS

Seong-Joo Lee et al., Pre-polarization enhancement by dynamic nuclear polarization in SQUID-based ultra-low-field nuclear magnetic resonance, Supercond. Sci. Technol., Oct. 5, 2010, vol. 23, pp. 115008-1~115008-6.

Clarke et al., "SQUID-Detected Magnetic Resonance Imaging in Microtesla Fields," The Annual Review of Biomedical Engineering, 2007, pp. 389-413, vol. 9, Annual Reviews, bioeng.annualreviews.org.

International Search Report for PCT/KR2011/004178 dated Feb. 10, 2012.

IPRP and Written Opinion for Application No. PCT/KR2011/004178 dated May 28, 2013.

* cited by examiner

ULTRA-LOW-FIELD NUCLEAR-MAGNETIC-RESONANCE DIRECT MYOCARDIAL ELECTRICAL ACTIVITY DETECTION METHOD AND ULTRA-LOW-FIELD NUCLEAR-MAGNETIC-RESONANCE DEVICE

CROSS-REFERENCE TO RELATED APPLICATIONS

This application is a continuation of and claims priority to PCT/KR2011/004178 filed on Jun. 9, 2011, which claims priority to Korea Patent Application No. 10-2010-0116596 filed on Nov. 23, 2010, the entireties of which are both hereby incorporated by reference.

BACKGROUND OF THE INVENTION

1. Field of the Invention

The present invention relates to ultra-low-field nuclear-magnetic-resonance devices and, more particular, to a direct myocardial electrical activity detection method using a nuclear-magnetic-resonance device.

2. Description of the Related Art

Many heart diseases are caused by reentry excitation or ectopic excitation of myocardium. Such a conduction abnormality develops atrial arrhythmia, tarchycardia, and heart failure that cause a stroke. Moreover, myocardial conduction abnormality is the mechanism of ventricular fibrillation that causes sudden cardiac death resulting from cardiac arrest. Conventionally, in order to detect myocardial conduction abnormality, a catheter electrode is inserted through aorta and vena cava of the thigh to measure endocardial potentials one by one while changing positions. Alternatively, a multi-channel electrode patch is attached to the epicardium during thoracotomy surgery to measure the endocardial potentials. A non-invasive method includes electrocardiogram (ECG) in which a plurality of electrodes are attached to thorax and limbs to measure a potential and magnetocardiogram (MCG) in which myocardial electrical activity is measured using an ultra-sensitive magnetic sensor such as a superconducting quantum interference device (SQUID) or an atomic magnetometer.

SUMMARY OF THE INVENTION

Embodiments of the present invention provide an ultra-low-field nuclear-magnetic-resonance myocardial electrical activity detection method for detecting abnormal electrical activity with periodicity such as reentry wave or ectopic excitation in myocardial electrical activity. According to the detection method, an external measurement bias magnetic field is lowered to set a resonance frequency of protons around the myocardium to a frequency of myocardial electric field variation resulting from the abnormal electrical activity. Thus, cardiac lesions are detected.

In an aspect of the present invention, an ultra-low-field nuclear-magnetic-resonance myocardial electrical activity detection method may include disposing a measurement target adjacent to high-sensitivity magnetic field measuring means inside magnetic shielding means; provide an external measurement bias magnetic field, corresponding to a proton magnetic resonance frequency (nuclear magnetic resonance frequency) corresponding to a frequency of periodic myocardial activity of a lesion desired to be measured, to the measurement target; and measuring a magnetic resonance signal generated from the measurement target using the high-sensitivity magnetic field measuring means.

In another aspect of the present invention, an ultra-low-field nuclear-magnetic-resonance device may include magnetic shielding means; high-sensitivity magnetic field measuring means disposed adjacent to a measurement target disposed inside the magnetic shielding means; and bias magnetic field generating means for providing an external measurement bias magnetic field, corresponding to a proton magnetic resonance frequency (nuclear magnetic resonance frequency) corresponding to a frequency of periodic myocardial activity of a lesion desired to be measured, to the measurement target. The high-sensitivity magnetic field measuring means may measure a magnetic resonance signal generated from the measurement target.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present invention.

DETAILED DESCRIPTION OF EMBODIMENTS

Figure 1:
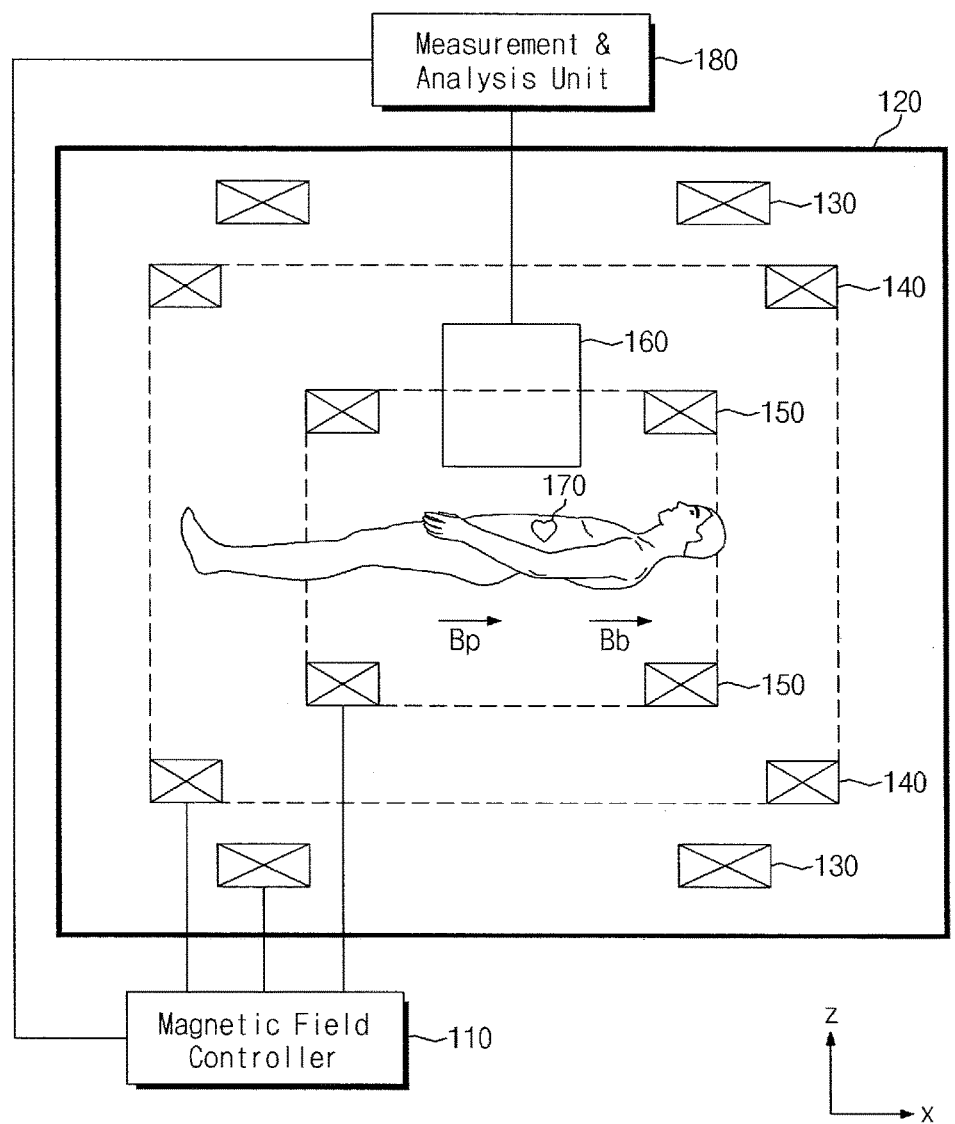
FIG. 1 illustrates an ultra-low-field nuclear-magnetic-resonance device according to an embodiment of the present invention.

An electrophysiology (EP) test is carried out to test myocardial electrical activity using a catheter. In the EP test, the catheter is inserted into the interior of human body and thus an electrode comes in contact with the endocardium to measure the myocardial electrical activity. This method is invasive and always involves the risk of surgery. Especially, a measurable part of the method is limited to the endocardium. In the case of passing through aorta and vena cava, an electrode cannot approach opposite atrium and ventricle without perforating the septum of the atrium and the ventricle. In order to place the electrode in position, a patient and a doctor have the burden of exposure to radioactivity during the treatment time. Furthermore, the method itself is unable to provide spatial information. Accordingly, means such as a magnetic position tracking device is required for spatial mapping of myocardial electrical activity.

In the case of an epicardial electrode array, there is a great burden of thoracotomy surgery and a high technology is required to attach an electrode. For this reason, the epicardial electrode array is not available in follow-up diagnosis or the like.

The spatial mapping of myocardial electrical activity using electrocardiogram (ECG) or magnetocardiogram (MCG) is current source estimation obtained by the solution of ill-posed inverse problem using a result of non-invasive measurement. Accordingly, there is a very large estimation error with respect to a deep current source or a current source whose constraint is not defined well. As a result, the ECG or the MCG is limited in clinical application.

An ultra-low-field nuclear-magnetic-resonance myocardial electrical activity detection method according to an embodiment of the present invention non-invasively measures and localizes myocardial activity which causes heart diseases such as reentry wave or ectopic excitation of heart. Thus, the detection method may provide development of new medical devices that help to research, diagnose, and treat the heart diseases.

The present invention will now be described more fully hereinafter with reference to the accompanying drawings, in which preferred embodiments of the present invention are shown. However, the present invention may be embodied in many different forms and should not be construed as limited to the embodiments set forth herein. Rather, these embodiments are provided so that this disclosure will be thorough and complete, and will fully convey the scope of the present invention to those skilled in the art. In the drawings, components are exaggerated for clarity. Like numbers refer to like elements throughout.

Figure 2:
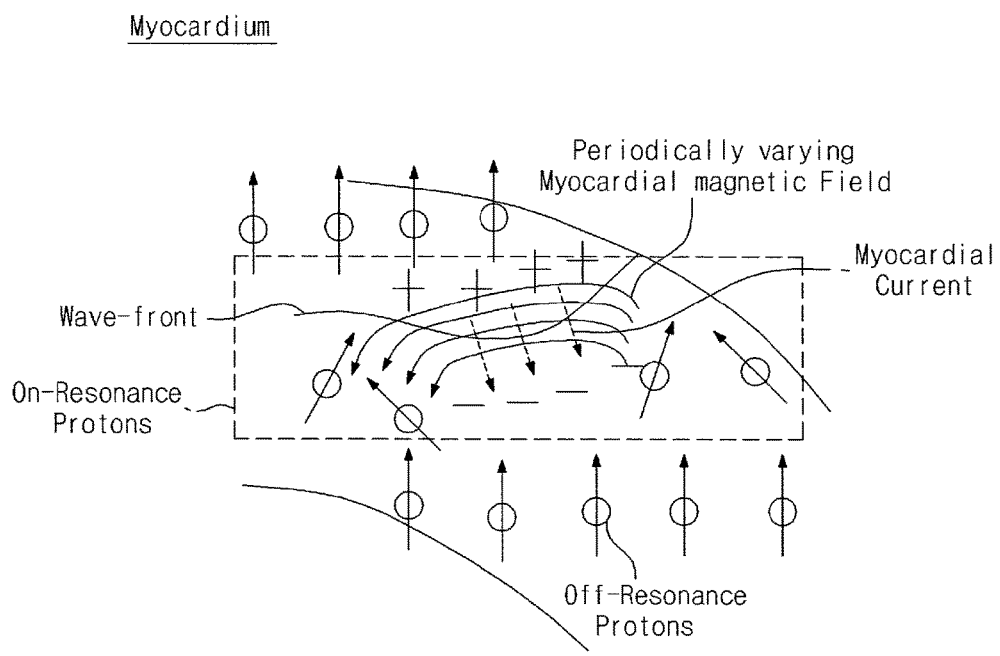
FIG. 2 illustrates the operation principle of the present invention.

FIG. 1 illustrates an ultra-low-field nuclear-magnetic-resonance device according to an embodiment of the present invention, and FIG. 2 illustrates the operation principle of the present invention.

Referring to FIGS. 1 and 2, the ultra-low-field nuclear-magnetic-resonance device includes magnetic shielding means 120, high-sensitivity magnetic field measuring means 160 disposed adjacent to a measurement target 170 disposed inside the magnetic shielding means 120, and bias magnetic field generating means 140 that provides, to the measurement target 170, an external measurement bias magnetic field Bb corresponding to a proton magnetic resonance frequency (nuclear magnetic resonance frequency) corresponding to a frequency of periodic myocardial activity of a lesion desired to be measured. The high-sensitivity magnetic field measuring means 160 measures a magnetic resonance signal generated from the measurement target 170.

The reentry wave or the ectopic excitation of heart has periodical features and local and repetitive features. That is, the myocardium is excited with a specific frequency (fs) according to lesion and focus. The myocardium of a depolarized area has a potential difference with respect to that of a repolarized area. The potential difference has a wave-front and generates myocardial current. The myocardial current generates a myocardial magnetic field Bm. A frequency (fm) of the myocardial magnetic field is identical to an excitation frequency (fs) of myocardial electricity such as reentry wave or ectopic excitation. The myocardial magnetic field has a strong influence on protons constituting the myocardium around the myocardial current. As a distance from the myocardial current source increases, the influence of the myocardial magnetic field is reduced.

The myocardial magnetic field of the characteristic frequency (fm) may be utilized as B1-RF magnetic field in typical magnetic resonance imaging (MRI). Thus, if a magnetic resonance phenomenon is spatially separated and measured, a position of reentry wave or ectopic excitation may be found out.

The ultra-low-field nuclear-magnetic-resonance device is different from a typical magnetic resonance imaging device in that a measurement bias magnetic field has a size of microtesla (μT) level and a biological generation phenomenon of the B1-RF magnetic field is used.

A resonance frequency depending on a gyromagnetic ratio of proton of water or the like around an excited cardiogram is about 42 MHz/T. For example, let it be assumed that a frequency (fs) of reentry wave in paroxysmal atrial fibrillation desired to be found corresponds to 42 Hz. In this case, the magnitude of an external measurement bias magnetic field Bb capable of causing magnetic resonance by absorbing the myocardial magnetic field Bm of the frequency (fs) corresponds to about 1 microTesla (μT).

Resonating protons around the myocardium generating the myocardial magnetic field Bm of frequency (fs) may form on-resonance protons under the external measurement bias magnetic field Bb. Non-resonating protons of myocardium excited at a frequency except for the frequency (fs) or myocardium far away from the myocardium excited at the frequency (fs) may form off-resonance protons. The magnitude of the external measurement bias magnetic field Bb is as small as one-millionth of existing MRI. The magnitude of the external measurement bias magnetic field Bb is smaller than the magnitude (about 50 μT) of the earth's magnetic field. Thus, a measurement target may be disposed inside the magnetic shielding means to eliminate the earth's magnetic field. The magnetic shielding means may be a magnetically shielded room or active magnetic shielding apparatus.

In a weak external measurement bias magnetic field Bb, it may be difficult to align proton spins. Accordingly, the practically measured intensity of a magnetic resonance signal is very low. Thus, a strong pre-polarization magnetic field Bp may be generated using pre-polarization means before measurement. The pre-polarization magnetic field Bp may pre-polarize a measurement target.

The protons may be aligned and the measurement target 170 may be polarized by the strong pre-polarization magnetic field Bp. A magnetic resonance precession frequency of proton corresponding to the magnitude of the external measurement bias magnetic field Bb is low. Accordingly, inductive measurement using the conventional coil where the intensity of a signal increases in proportion to a frequency of measurement signal is unable to provide a signal of sufficient intensity. Thus, the high-sensitivity magnetic field measuring means 160 may be a superconducting quantum interference device (SQUID) or an optically pumped atomic magnetometer whose measurement sensitivity is independent of signal frequency.

The bias magnetic field generating means 140 may generate the external measurement bias magnetic field Bb and be a conventional resistive coil. The bias magnetic field generating means 140 may be disposed inside the magnetic field shielding means 120. The bias magnetic field generating means 140 may scan the intensity of the magnetic field. Thus, the magnitude of the external measurement bias magnetic field Bb may correspond to an excitation frequency (fs) of myocardial electricity desired to be measured. For example, the external measurement bias magnetic field Bb may be applied continuously or in form of pulse in the x-axis direction.

A pre-polarization means 150 may generate a pre-polarization magnetic field Bp to pre-polarize the measurement target 170. The pre-polarization means 150 may reinforce the nuclear polarization of the measurement target 170 by using dynamic nuclear polarization. The pre-polarization means 150 may be a conventional resistive coil or a superconducting coil. The pre-polarization means 150 may be disposed inside the magnetic shielding means 120. In addition, the pre-polarization means 150 may be disposed inside the bias magnetic field generating means 140 while surrounding the measurement target 170. The pre-polarization magnetic field Bp may be applied in the x-axis direction by pulse.

A gradient magnetic field generating means 130 provides a gradient magnetic field to the measurement target 170. Thus, a nuclear resonance signal generated from the measurement target 170 may be localized. The gradient magnetic field generating means 130 may be a conventional resistive coil. The gradient magnetic field generating means 130 may be disposed between the measurement target 170 and the magnetic shielding means 120.

The magnetic field measuring means 160 is disposed adjacent to the measurement target 170 and obtains the magnetic resonance signal emitted from the measurement target 170. An output signal of the magnetic field measuring means 160 is provided to a measurement and analysis unit 180.

The measurement and analysis unit 180 may provide a frequency (fs) and a position of reentry wave in paroxysmal atrial fibrillation.

The magnetic field controller 110 may apply various magnetic fields to the measurement target 170 in synchronization with the measurement and analysis unit 180. The magnetic field controller 110 may control the pre-polarization means 150, the bias magnetic field generating means 140, and the gradient magnetic field generating means 130 according to a series of sequence.

Figure 3:
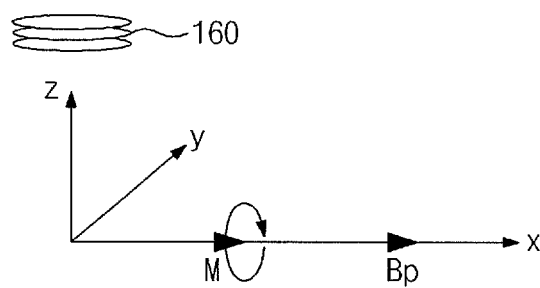
FIG. 3 illustrates the operation principle of an ultra-low-field nuclear-magnetic-resonance device according to an embodiment of the present invention.
Figure 3:
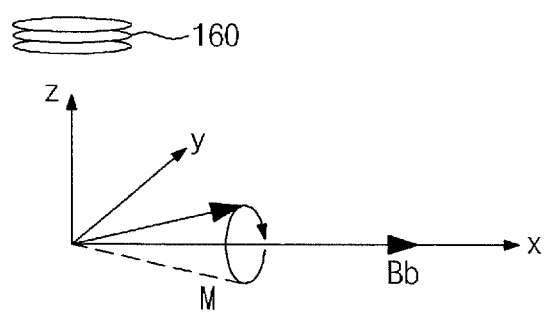

FIG. 3 illustrates the operation principle of an ultra-low-field nuclear-magnetic-resonance device according to an embodiment of the present invention.

Referring to FIG. 3, a high-sensitivity magnetic field measuring means 160 is disposed to be sensitive to a magnetic field parallel to the z-axis direction on the basis of a Cartesian coordinate system. Both a pre-polarization magnetic field Bp generated by pre-polarization means and a bias magnetic field Bb generated by bias magnetic field generating means may be applied to be parallel to the x-axis direction. In this case, nuclear spin of protons in a measurement target are aligned in the x-axis direction to establish magnetization M. As soon as the pre-polarization magnetic field is turned off, the measurement starts. In this case, the established magnetization M rotates on the x-axis that is direction of an external measurement bias magnetic field Bb. If there is no myocardial activity causing magnetic resonance, there is originally no magnetization component of the z-axis direction. Hence, magnetic field variation of the z-axis direction does not occur and a signal is not measured.

However, in the case where a reentry wave is periodically generated at a magnetic resonance frequency that is in proportion to the external measurement bias magnetic field Bb by myocardial failure and the direction of a myocardial magnetic field Bm of alternating current (AC) generated from variation of cardiac current is the y-axis or z-axis direction, the magnetization M aligned in the x-axis direction is inclined due to a magnetic resonance phenomenon. The inclined magnetization M rotates on the x-axis that is the direction of the external measurement bias magnetic field Bb. Therefore, a z-axis directional component of the varying magnetization is formed to generate a z-axis directional magnetic field. The z-axis directional magnetic field may be measured by the high-sensitivity magnetic field measuring means 160.

That is, according to a direction or a frequency of myocardial electrical activity desired to be measured, the applied external measurement bias magnetic field Bb may be adjusted or scanned to directly measure myocardial failure. Magnetic resonance imaging (MRI) methods using a well-known gradient magnetic field may be applied to obtain spatial position information.

Atrial fibrillation, which is a kind of atrial arrhythmia, results from the generation of a reentry wave caused by aging or deformation of atrial myocardium. Especially when a causing part is found, by finding a spot where a high-frequency f wave (periodic waveform) propagates through a Catheter electrode, a treatment is carried out by means of RF ablation or freezing. However, it is difficult to perform measurement using a probe that contacts parts one by one and it takes a very long time to perform the measurement. Moreover, an invasive test acts as a burden on follow-up diagnosis.

If the configuration of the inventive concept is applied to this case, a spot where a myocardial high frequency fm is generated may be imaged very safely and effectively.

Figure 4:
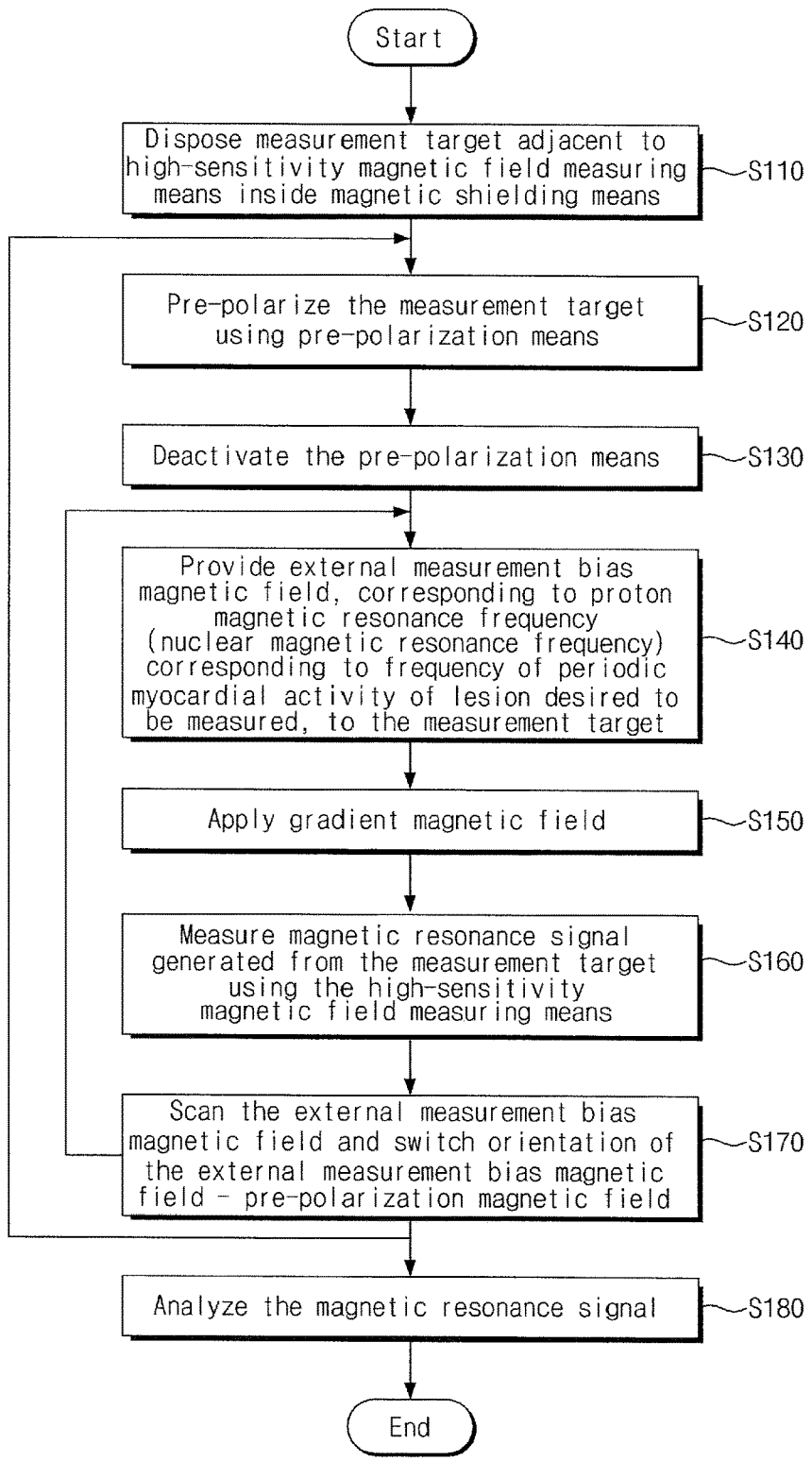
FIG. 4 is a flowchart illustrating an ultra-low-field nuclear-magnetic-resonance myocardial electrical activity detection method according to an embodiment of the present invention.

FIG. 4 is a flowchart illustrating an ultra-low-field nuclear-magnetic-resonance myocardial electrical activity detection method according to an embodiment of the present invention.

Referring to FIG. 4, the ultra-low-field nuclear-magnetic-resonance myocardial electrical activity detection method includes disposing a measurement target adjacent to high-sensitivity magnetic field measuring means inside magnetic shielding means (S110), providing an external measurement bias magnetic field, corresponding to a proton magnetic resonance frequency (nuclear magnetic resonance frequency) corresponding to a frequency of periodic myocardial activity of a lesion desired to be measured, to the measurement target (S140), and measuring a magnetic resonance signal generated from the measurement target using the high-sensitivity magnetic field measuring means (S160).

A measurement target is disposed adjacent to a high-sensitivity magnetic field measuring means inside magnetic shielding means (S110). A pre-polarization magnetic field is generated to polarize the measurement target (S120). The pre-polarization means is deactivated to remove the pre-polarization magnetic field (S130).

The bias magnetic field generating means generates an external measurement bias magnetic field. The external measurement bias magnetic field is applied to the measurement target under the state that the pre-polarization magnetic field is removed (S140). However, the application of the external measurement bias magnetic field is independent of the ON-OFF order of the pre-polarization magnetic field. The external measurement bias magnetic field may always be applied without variation. The external measurement bias magnetic field corresponds to a proton magnetic resonance frequency (nuclear magnetic resonance frequency) corresponding to a frequency of periodic myocardial activity of a lesion desired to be measured.

A gradient magnetic field is applied to the measurement target (S150). A magnetic resonance signal generated from the measurement target is measured using the high-sensitivity magnetic field measuring means (S160). The high-sensitivity magnetic field measuring mean may be a high-sensitivity magnetic sensor such as a superconducting quantum interference device (SQUID) or an optically pumped atomic magnetometer.

The external measurement bias magnetic field is scanned according to a frequency of a signal desired to be measured and the orientation of the external measurement bias magnetic field—the pre-polarization magnetic field is switched (S170).

The magnetic resonance signal is analyzed to provide a frequency and/or a position of periodic myocardial activity of the lesion (S180).

A detailed method of measurement may vary depending on the orientation and application time of each magnetic field and a phenomenon desired to be measured.

The intensity of a magnetic resonance signal according to an embodiment of the present invention is in proportion to the magnitude of pre-polarization. Although a magnetic field generating device such as a typical coil is used, a signal may be raised by injecting magnetization-enhanced water into the blood vessel. The magnetization of the water is enhanced by means of dynamic nuclear polarization.

According to an ultra-low-field nuclear-magnetic-resonance myocardial electrical activity detection described so far, an occurrence position of cardiac reentry wave or ectopic excitation may be searched very accurately by a non-invasive method. Thus, the detection method can be applied to safety and convenient medical diagnosis. Long and dangerous procedure and exposure to radiation of not only a patient but also a doctor can be reduced. Since the detection method can be used for diagnosis for treatment and be used for follow-up diagnosis, the detection method can be applied to develop new and innovative medical equipments.

Although the present invention has been described in connection with the embodiment of the present invention illustrated in the accompanying drawings, it is not limited thereto. It will be apparent to those skilled in the art that various substitutions, modifications and changes may be made without departing from the scope and spirit of the present invention.

What is claimed is:

1. An ultra-low-field nuclear-magnetic-resonance device comprising:
   a magnetic shielding room configured for reducing Earth's magnetic field;
   a high-sensitivity magnetic field sensor disposed adjacent to a measurement target disposed inside the magnetic shielding room; and
   a bias magnetic field generating coil disposed inside the magnetic shielding room, the bias magnetic field generating coil being configured for providing an external measurement bias magnetic field to the measurement target, the external measurement bias magnetic field corresponding to a proton magnetic resonance frequency (nuclear magnetic resonance frequency) corresponding to a frequency of periodic myocardial activity of a lesion desired to be measured,
   wherein the high-sensitivity magnetic field sensor measures a magnetic resonance signal generated from the measurement target;
   wherein the bias magnetic field generating coil scans the external measurement magnetic field according to a frequency of a signal desired to be measured; and
   wherein an orientation of the external measurement bias magnetic field and a pre-polarization magnetic field is switched.

2. The ultra-low-field nuclear-magnetic-resonance device of claim 1, further comprising:
   a pre-polarization coil configured for generating the pre-polarization magnetic field by pre-polarizing the measurement target;
   wherein the pre-polarization coil is disposed inside the magnetic shielding room.

3. The ultra-low-field nuclear-magnetic-resonance device of claim 1, further comprising:
   a gradient magnetic field generating coil configured for providing a gradient magnetic field to the measurement target;
   wherein the gradient magnetic field generating coil is disposed inside the magnetic shielding room.

* * * * *